United States Patent [19]

Bloom, Jr.

[11] Patent Number: 4,993,436
[45] Date of Patent: Feb. 19, 1991

[54] ASPIRATING AND VOLATILIZING LIQUID DISPENSER

[76] Inventor: Walter L. Bloom, Jr., 1281 Beech Haven Rd., Atlanta, Ga. 30324

[21] Appl. No.: 454,275

[22] Filed: Dec. 21, 1989

[51] Int. Cl.$^5$ .............................................. A24F 47/00
[52] U.S. Cl. .................................. 131/335; 131/273; 128/200.14; 128/200.21
[58] Field of Search ...................... 131/273, 335, 337; 128/200.14, 200.21

[56] References Cited

U.S. PATENT DOCUMENTS

| | | | |
|---|---|---|---|
| 4,657,032 | 4/1987 | Dorr et al. | 131/337 X |
| 4,774,971 | 10/1988 | Vietan | 131/273 |
| 4,776,353 | 10/1988 | Lilja et al. | 131/273 X |
| 4,800,903 | 1/1989 | Ray et al. | 131/273 |
| 4,813,437 | 3/1989 | Ray | 131/273 |
| 4,848,376 | 7/1989 | Lilja et al. | 131/335 X |
| 4,911,181 | 3/1990 | Vromen et al. | 131/273 |

Primary Examiner—V. Millin
Assistant Examiner—Jennifer L. Doyle
Attorney, Agent, or Firm—B. J. Powell

[57] ABSTRACT

A dispenser comprising a container and a mouthpiece is adapted to deliver a volatilizable liquid orally to the user. A volatilizing chamber is defined between the liquid reservoir in the container and the drawing passage in the mouthpiece through which the user inhales. A permeable fluid barrier separates the liquid in the reservoir from the open pore material which fills the volatilizing chamber and limits the amount of liquid which can be aspirated through the open pore material to the user. A vent passage in parallel with the fluid barrier when uncovered and open allows air to be drawn through the open pore material to volatilize any liquid retained thereon. When covered and closed, the vent passage allows liquid to be aspirated from the reservoir through the permeable fluid barrier, the volatilizing chamber, and the mouth piece and into the user's mouth.

14 Claims, 2 Drawing Sheets

U.S. Patent  Feb. 19, 1991  Sheet 1 of 2  4,993,436
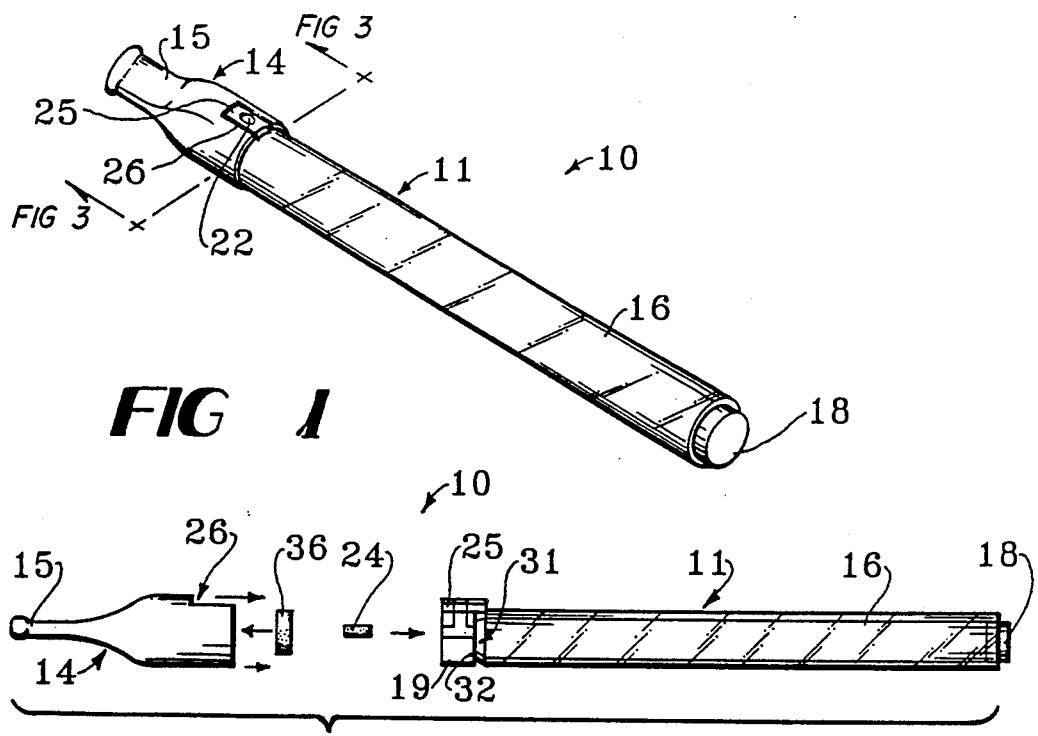
FIG. 1
FIG. 2
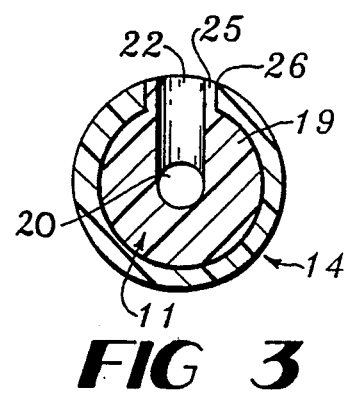
FIG. 3
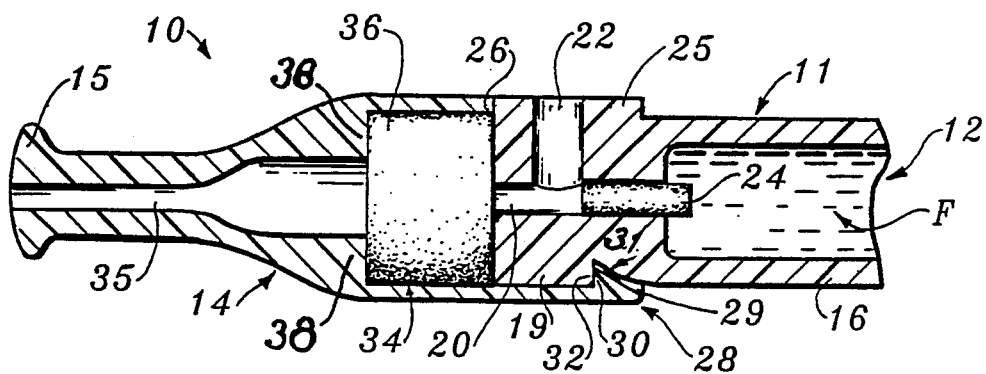
FIG. 4

ASPIRATING AND VOLATILIZING LIQUID DISPENSER

BACKGROUND OF THE INVENTION

This invention relates generally to dispensing devices and more particularly to a device for controllably dispensing and volatilizing liquid by the user sucking or drawing on the device.

Various types of fluid dispensing devices in which the user inhales or draws on the device to dispense the fluid have been available for many years. Many of these dispensing devices have been embodied in smoking substitute devices so that the user has an alternative to smoking. A representative listing of prior art devices is set forth below.

| U.S. Pat. No. | INVENTOR | ISSUE DATE |
| --- | --- | --- |
| 2,764,154 | Murai | 9/25/56 |
| 3,320,953 | Rindner | 5/23/67 |
| 3,365,102 | Castleberry | 1/23/68 |
| 3,884,246 | Walker | 5/20/75 |
| 4,083,372 | Boden | 4/11/78 |
| 4,149,548 | Bradshaw | 4/17/79 |
| 4,569,136 | Loring | 2/11/86 |
| 4,657,032 | Dorr et al. | 4/14/87 |

Many of these devices have included liquids which contain various extracts or other tastes to simulate products from smoking for the use.

SUMMARY OF THE INVENTION

In contrast with all such prior cited devices, the invention disclosed herein provides the user with a novel, multiple mode method of dispensing liquids orally under simple manual control. Although the invention is similar in size and appearance to a cigarette or a small cigar, and is extremely economical in design, its unique dispensing method and mechanism enables the user to consume one full reservoir of liquid over an extended interval or one or more hours of continuous operation. Additionally, the invention's dispensing mechanism is readily adaptable to a wide range of uniquely flavored liquid solutions varying both in viscosity and flavor intensity.

The dispenser includes a container which defines a closed fluid reservoir therein and a mouthpiece which is connected to the container with a bit adapted to be grasped in the user's mouth. The bit defines a passage therethrough in communication with a volatilizing chamber formed between the mouthpiece and the container. A fluid barrier of limited permeability connects the fluid in the reservoir with the volatilizing chamber so that fluid will be aspirated from the reservoir when a sufficient pressure differential is imposed across the barrier. A vent passage connects the volatilizing chamber with the ambient air in parallel with the fluid barrier so that air can be drawn through the vent passage into the volatilizing chamber without imposing a sufficient pressure differential across the fluid barrier to cause fluid to be aspirated from the reservoir into the volatilizing chamber. To aspirate fluid from the reservoir into the volatilizing chamber and the bit passage, the vent passage is blocked while the user draws through drawing passage in the bit. An open pore material is located in the volatilizing chamber between the drawing passage to the user's mouth and both the vent passage and the fluid barrier so that fluid from the reservoir must pass through the open pore material to reach the user's mouth. Because the reservoir is sealed with the exception of the permeable fluid barrier, closing the vent passage allows the user's sucking on the bit to aspirate liquid from the fluid reservoir while creating a vacuum therein. This induced vacuum serves to control the total volume of liquid which can be aspirated from the reservoir at any one time without allowing the pressure in the reservoir to against return to atmospheric pressure.

These and other features and advantages of the invention disclosed herein will become more clearly understood upon consideration of the following detailed description and accompanying drawings wherein like characters of reference designate corresponding part through the several views and in which:

BRIEF DESCRIPTION OF THE DRAWINGS

FIG. 1 is a perspective view illustrating a liquid dispenser embodying the invention;

FIG. 2 is an exploded elevational view showing the various components of the invention;

FIG. 3 is a transverse cross-sectional view taken along line 3—3 in FIG. 1;

FIG. 4 is an enlarged longitudinal cross-sectional view of the container/mouthpiece connection of the dispenser;

Figure 5:
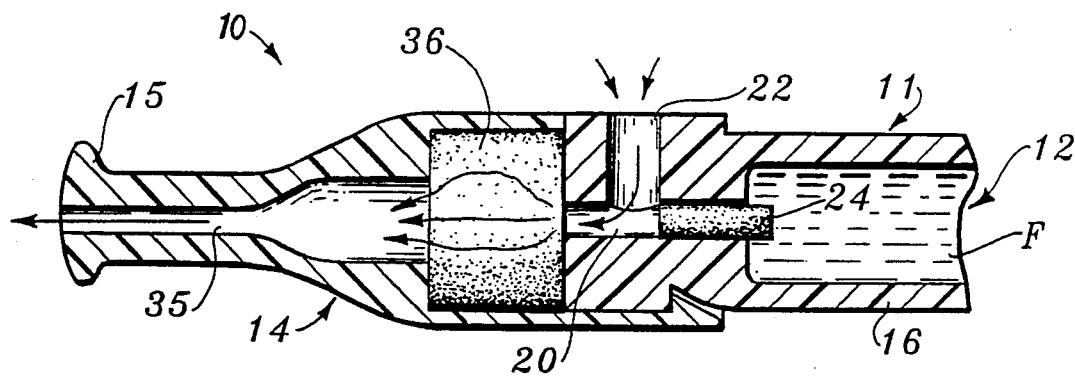
FIG. 5 is a view similar to FIG. 4 showing the invention in the volatilizing mode.

These figures and the following detailed description disclose specific embodiments of the invention, however, it is to be understood that the inventive concept is not limited thereto since it can be incorporated in other forms.

DETAILED DESCRIPTION OF ILLUSTRATED EMBODIMENTS

The dispenser 10 seen in the drawings includes a container 11 defining a liquid reservoir 12 therein to carry the liquid to be dispensed. A mouthpiece 14 is provided to fit onto the end of the container 11 and defines a bit 15 thereon adapted to be held in the user's mouth in conventional manner.

The container 11 includes a reservoir 12 for liquid, said reservoir defined by an elongate tubular side wall 16, which in turn is closed at one end by a plug 18 and at the other end by an integral cylindrical end section 19. The end section 19 defines a longitudinally extending central passage 20 therethrough which opens into the reservoir 12.

A vent passage 22 extends from the outside of the end section 19 into the central passage 20 intermediate its ends. Thus, it will be seen that the end of passage 20 opening onto the projecting end of section 19 communicates with the liquid F in the reservoir 12 and with the ambient air in parallel as will become more apparent. A raised locating section 25 is provided around the end of the vent passage opening on the outside of the end section 19 which serves to rotationally locate the mouthpiece 14 on the container 11 as will become more apparent.

A liquid barrier 24 is inserted into the central passage 20 between the vent passage 22 and the reservoir 12 to retain the liquid F within the reservoir 12 until a prescribed pressure differential is imposed across the barrier as will become more apparent. The purpose of the barrier 24 is virtually to prevent the flow of liquid F from the reservoir 12 as long as the vent passage 22 is open but to allow liquid F to pass therethrough when the vent passage 22 is closed and a lower pressure is imposed in the passage 20 than in the reservoir 12 to create a sufficient pressure differential across the barrier 4.

The end of the mouthpiece 14 opposite the bit 15 defines an enlarged recess therein sized to fit over the end section 19 of the container 11. A cutout 26 is also defined through the side of the mouthpiece 14 to fit around the locating section 25 so that the vent passage 22 is left open and the mouthpiece 14 will not rotate on the container 11. An inwardly directed latching lip 28 is formed on the end of the mouthpiece 14 onto which the recess opens. The lip 28 has an inwardly tapering surface 29 facing the container 11 with a locking surface 30 oriented normal to the common mouthpiece and container centerlines $CL_1$.

A complementary locking groove 31 is formed around the end section 19 normal to the centerline $CL_1$ which defines a locking surface 32 thereon facing oppositely to that of the locking surface 30 on the mouthpiece 14. Thus, it will be seen that, as the open end of the mouthpiece 14 is forced onto the end section 19 of the container 11, the locking lip 28 can expand because of the cutout 26 in the mouthpiece 14 and the resiliency of the material of the mouthpiece which may be a plastic. When the locking lip 28 drops into the locking groove 31, the locking surfaces 30 and 32 engage and lock the mouthpiece onto the container.

When the mouthpiece 14 is locked onto the container 11, the recess in the mouthpiece and the end section of the container form a volatilizing chamber 34 therebetween. The chamber 34 communicates with a drawing passage 35 through the bit 15 at one end and with the central passage 20 at its other end. Thus, it will be seen that the user drawing on the bit will draw air through the vent passage 22 and the volatilizing chamber 34 when the vent passage is open. Likewise, closing the vent passage and drawing on the bit will create a sufficient pressure differential across the liquid barrier 24 to force liquid F from the reservoir 12 into the volatilizing chamber. The liquid barrier 24 is selected to permit enough liquid flow therethrough to give the user the desired taste sensation when the vent passage is closed, yet not to permit enough fluid flow therethrough to overpower the user's taste.

To provide a large surface area of liquid F to be volatilized as air is drawn into the user's mouth through the vent passage and the volatilizing chamber 34, an open pore material 36 is fitted into the chamber 34. Appropriate abutments 38 may be provided in the chamber 34 to hold the material 36 in place.

Various designs may be used for the liquid barrier 24 as long as it meets the above criteria. For instance, small holes in the end section 19 may be used with the necessary small diameter. Alternatively, a porous plug may be used for the barrier 24 and this version is illustrated. The length, diameter and porosity of the porous plug 24 is selected to give the required volumetric flow rate of the liquid in the reservoir 12 as will become more apparent. The porous plug 24 may have different structures, however, plugs 24 having an open cell pore structure have been found satisfactory. In particular, plastic porous plugs with an open cell omnidirectional pore structural have been found particularly satisfactory. The particular pore characteristics and size will, of course, depend on the liquid being used. For flavored aqueous solutions, a porous plug 24 with a 20-240 micron pore size (100-120 micron preferred) and a diameter of about 0.125 inch with a void fraction greater than about 35% has been found satisfactory. The length of the plug 24 should be short enough to permit the liquid to pas through the porous plug and along the passage into the volatilizing chamber 34 to place liquid F in the open pore material 36 during the time that the user will suck on the dispenser with the vent passage 22 closed. A length of about 0.125-0.250 inches has been found satisfactory. While the diameter of the passage 20 is not critical, a diameter slightly smaller than the porous plug 24 has been found satisfactory.

The size of the liquid reservoir 12 is not critical and may take a number of forms. It is anticipated that the diameter and length of the container 11 will correspond to that of a cigarette or small cigar. While these dimensions may vary, a liquid reservoir 12 of about 0.375 inch diameter and a length of about three inches has been found satisfactory. These dimensions provide a sufficient volume of liquid for extended periods of use. While the total time provided will depend on the level of consumption desired by the user, typically, more than an hour of use will be attained.

The vent passage 22 may extend in any direction and is illustrated as extending perpendicular to the axis of the dispenser to open onto the outside of the end section 19 and communicate with the volatilizing chamber 34 in parallel with the liquid barrier 24. The vent passage 22 serves to allow the user to suck air through the material 36 to volatilize the liquid thereon. The diameter of the vent passage 22 may be varied as long as the air flow velocity therethrough is sufficiently low to keep the pressure differential across the barrier 24 below that which will cause the liquid to flow into the material 36 while vent passage 22 is open. It is anticipated that the vent passage diameter may vary between 0.125 and 0.135 inches.

It will be appreciated that side wall 16 may be made out of a rigid or flexible material, probably plastic. When the side wall 16 is rigid, the user can withdraw liquid from within the reservoir until the internal suction equals that applied by the user in the passage 20. When the user releases the vent passage 22, air can then flow back through the porous plug 24 to equalize the pressure within the reservoir 12 to atmospheric pressure. After this occurs, the user can again withdraw the liquid from within the reservoir 12.

When the side wall 16 is flexible, the user can additionally force liquid through the porous plug 24 by pinching the side walls together. The porous plug 24 still continues to regulate the flow of liquid from the reservoir 12.

The open pore material 36 may be any of a number of materials. One material which has been found satisfactory is a reticulated plastic foam with a void volume of about of 85-95%. Also, natural fibers such as cotton may be used. One elastomeric reticulated foam for the open pore material 36 is one composed of a polyurethane. More than one version of polyurethane foams suitable herein are available commercially. One such "typical" suitable polyurethane foam is described in U.S. Pat. No. 3,171,820 to Volz which has been dewindowed to remove the membranous elastomer from the cell faces to a reticulated foam.

The reticulated foam used in the present invention will be in the form of a cylindrical plug. While the diameter and thickness may be varied, a diameter of about 0.4 inch and a thickness of about 0.25-0.50 inches has been found satisfactory.

OPERATION

The invention has two distinct modes of operation in which the user actively sucks on the end of the mouthpiece 14. These two modes are the aspirating and volatilizing modes, respectively. In common usage, these two sucking modes are separated automatically by a third transient venting mode in which the user does not suck on the end of the mouthpiece 14.

Figure 6:
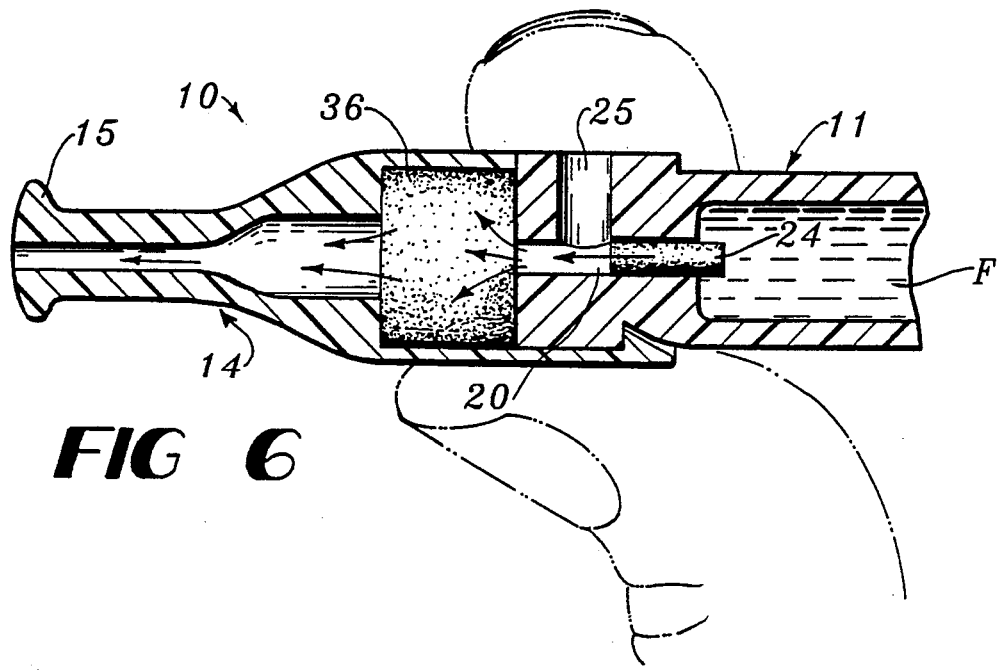
FIG. 6 is a view similar to FIG. 4 showing the invention in the aspirating mode.

In aspirating mode, the user covers the vent passage 22 with his finger, as illustrated in FIG. 6, and sucks on the bit 15 to force liquid through the fluid barrier 24 to the material 36. In this mode, some of the liquid is aspirated through the material 36 and into the user's mouth as an aerosol, while the remainder is retained by the material 36 for subsequent aspiration and volatilization.

Figure 7:
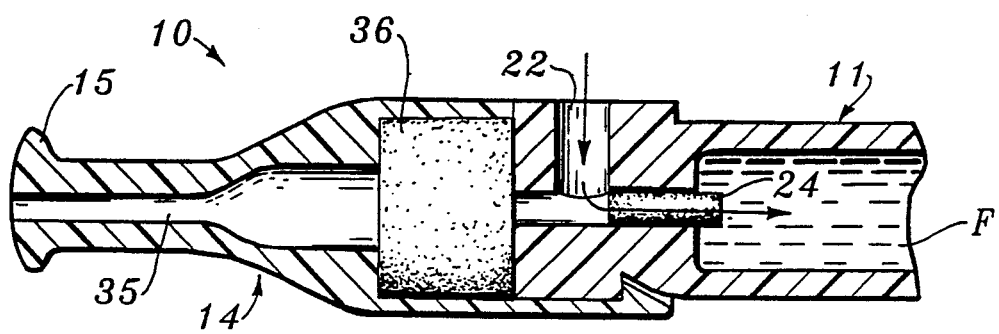
FIG. 7 is a view similar to FIG. 4 showing the invention in the transient venting mode.

By uncovering the vent passage 22, the user automatically enters the transient venting mode. In this transient mode, as illustrated in FIG. 7, the invention momentarily draws air back into the liquid reservoir 12. This automatic back drafting raises the pressure in the reservoir 12 back to the atmospheric pressure. Subsequently, in aspirating mode, the user may again draw more liquid from the reservoir 12.

In volatilizing mode, the user leaves the vent passage 22 uncovered, and sucks air through the open pore material 36 in order to volatilize any liquid retained thereon. In this mode, as illustrated in FIG. 5, the invention provides the user with the sensation of flavor even though the user is not sucking liquid through the fluid barrier 24 from the reservoir 12. It is anticipated that user commonly may operate the invention in this mode more than 95% of the time.

What is claimed is:

1. A dispenser adapted to deliver a liquid orally to a user and to volatilize same comprising:
    a container defining an enclosed liquid reservoir therein to contain the liquid to be dispensed;
    a mouthpiece operatively associated with said container and defining a bit thereon adapted to be grasped in the user's mouth, said bit defining a drawing passage therethrough so that the user can suck fluids therethrough by inhaling;
    said container and said mouthpiece defining an enclosed volatilizing chamber and a vent passage from said volatilizing chamber to the ambient air;
    a fluid barrier of limited permeability connecting said liquid reservoir with said volatilizing chamber so that said vent passage communicates with said volatilizing chamber in parallel with said liquid barrier; and,
    an open pore material within said volatilizing chamber located so that air sucked into said drawing passage from said vent passage must pass through said open pore material and so that some of the liquid sucked from said liquid reservoir will be retained in said open pore material to be volatilized before passage into the user's mouth through said drawing passage,
    whereby the user can inhale the volatilized liquid from said open pore material by sucking on the bit with the vent passage open to the ambient air and can aspirate the liquid directly into the user's mouth while replenishing the liquid in said open pore material by selectively closing said vent passage and sucking on the drawing passage to impose a sufficient pressure differential across said liquid barrier to cause liquid to be aspirated from said liquid reservoir until the pressure across said liquid barrier equalizes.

2. The dispenser of claim 1 wherein said liquid barrier is a porous plug.

3. The dispenser of claim 2 wherein said vent passage has a diameter at least as great as the diameter of said porous plug.

4. The dispenser of claim 2 wherein said porous plug defines a pore size of 20-240 microns and a void fraction of at least 35%.

5. The dispenser of claim 4 wherein said porous plug has a pore size of 100-120 microns and a void fraction of 40-50%.

6. The dispenser of claim 5 wherein said open pore material is an open cell reticulated foam.

7. The dispenser of claim 6 wherein said reticulated foam has a void fraction of at least 90%.

8. The dispenser of claim 7 wherein said vent passage has a diameter at least as great as the diameter of said porous plug.

9. The dispenser of claim 1 wherein said open pore material is an open cell reticulated foam.

10. The dispenser of claim 9 wherein said reticulated foam has a void fraction of at least 90%.

11. A dispenser adapted to deliver a liquid orally to a user and to volatilize same comprising:
    a container defining an enclosed liquid reservoir therein to contain the liquid to be volatilized;
    a mouthpiece;
    connection means for connecting said mouthpiece to said container;
    said mouthpiece defining a recess therein cooperating with said container to define an enclosed volatilizing chamber when said mouthpiece is connected to said container;
    said container including an end section connected to said mouthpiece and defining a central passage therethrough communicating with said volatilizing chamber at one end and with said liquid reservoir at its other end, said end section further defining a vent passage from said central passage intermediate its ends to the ambient air;
    said mouthpiece defining a bit thereon adapted to be grasped in the user's mouth, said bit defining a drawing passage therethrough to said volatilizing chamber so that the user can such air therethrough by inhaling;
    a liquid barrier of limited permeability filling said central passage for at least a portion of its length between said vent passage and said liquid reservoir to connect said liquid reservoir with said volatilizing chamber so that said vent passage communicates with said volatilizing chamber in parallel with said liquid barrier; and,
    an open pore material within said volatilizing chamber located so that air sucked into said drawing passage from said vent passage must pass through said open pore material and so that liquid sucked from said liquid reservoir will pass through said open pore material so that some of the liquid will be retained in said open pore material to be volatilized before passage into the user's mouth through said drawing passage, whereby the user can inhale the volatilized liquid from said open pore material by inhaling with the vent passage open to the ambient air and can replenish the liquid on said open pore material by selectively closing said vent passage and sucking on the drawing passage to impose a sufficient pressure differential across said liquid barrier to cause liquid to be withdrawn from said liquid reservoir until the pressure across said liquid barrier equalizes.

12. The dispenser of claim 11 wherein said connection means includes a locking lip on said mouthpiece about said recess and a complementary groove on said container to engage said lip to maintain said mouthpiece on said container.

13. The dispenser of claim 11 further including locating means to rotationally locate said mouthpiece with respect to said container.

14. A method of selectively aspirating and volatilizing a liquid into a user's mouth comprising the steps of:
 (a) maintaining the liquid in a closed chamber;
 (b) connecting the liquid in the chamber to the user's mouth through a liquid barrier of limited permeability in series with an open pore material so that liquid passing out of said chamber must pass through said open pore material before it reaches the user's mouth; and
 (c) also connecting the ambient air to the user's mouth through the open pore material via a vent passage in parallel with said liquid barrier so that the user can block the vent passage to aspirate liquid directly from the chamber and alternately can vaporize liquid retained in the open pore material without significant aspiration of the liquid from the closed chamber by leaving the vent unblocked.

* * * * *